(12) United States Patent
Bellifemine (10) Patent No.: US 8,712,555 B2
(45) Date of Patent: Apr. 29, 2014

(54) PORTABLE DEVICE FOR TREATING INSECT BITES AND THE LIKE

(75) Inventor: Francesco Bellifemine, Varese (IT)

(73) Assignee: Tecnimed S.R.L., Vedano Olona (IT)

( * ) Notice: Subject to any disclaimer, the term of this patent is extended or adjusted under 35 U.S.C. 154(b) by 77 days.

(21) Appl. No.: 12/514,521

(22) PCT Filed: Aug. 21, 2007

(86) PCT No.: PCT/IB2007/002473
§ 371 (c)(1),
(2), (4) Date: Sep. 21, 2009

(87) PCT Pub. No.: WO2008/059326
PCT Pub. Date: May 22, 2008

(65) Prior Publication Data
US 2010/0042196 A1 Feb. 18, 2010

(30) Foreign Application Priority Data
Nov. 13, 2006 (IT) .............................. MI2006A2178

(51) Int. Cl.
*A61N 1/00* (2006.01)
(52) U.S. Cl.
USPC ........................................................ 607/145
(58) Field of Classification Search
USPC .............................. 607/50, 115, 145, 149, 150
See application file for complete search history.

(56) References Cited

U.S. PATENT DOCUMENTS

| | | | | |
|---|---|---|---|---|
| 3,758,827 A * | 9/1973 | Schroder et al. | ............... | 361/247 |
| 3,826,952 A * | 7/1974 | Iwasaki et al. | ................ | 361/247 |
| 3,829,737 A * | 8/1974 | Johnsson | ...................... | 361/247 |
| 4,297,609 A * | 10/1981 | Hirao et al. | ................... | 310/339 |
| 4,315,180 A * | 2/1982 | Kondo et al. | ................. | 310/319 |
| 4,703,160 A | 10/1987 | Narishima et al. | | |
| 4,741,347 A * | 5/1988 | Robert et al. | ................ | 607/150 |
| 4,926,880 A * | 5/1990 | Claude et al. | ................. | 607/148 |
| 4,982,743 A * | 1/1991 | Pierson | ......................... | 607/150 |
| 5,235,990 A * | 8/1993 | Dempsey | ....................... | 607/145 |
| 5,496,356 A * | 3/1996 | Hudz | .............................. | 607/72 |
| 5,800,504 A * | 9/1998 | Bellifemine | .................. | 607/145 |
| 2003/0164662 A1 | 9/2003 | Amoros et al. | | |
| 2009/0222060 A1* | 9/2009 | Boyd et al. | ...................... | 607/48 |

FOREIGN PATENT DOCUMENTS

| | | |
|---|---|---|
| EP | 0788809 A | 8/1997 |
| WO | 03074939 A | 9/2003 |

* cited by examiner

Primary Examiner — Christopher D Koharski
Assistant Examiner — Roland Dinga
(74) Attorney, Agent, or Firm — Pearne & Gordon LLP (57) ABSTRACT

A portable device for treating the bites or stings of insects and harmful creatures, comprising:—a piezoelectric element (2) capable of producing a predetermined difference in electrical potential;—an actuating element (3) operable by a user and associated with said piezoelectric element (2) to impart to it a predetermined state of stress/deformation;—a discharge area (4) electrically connected to the piezoelectric element (2) and positionable in proximity to an area of a patient which has been bitten/stung to impart to it an electrical discharge generated by said difference in electrical potential; characterised in that it comprises furthermore a monolithic containing body (5) capable of housing the piezoelectric element (2), the actuating element (3) and the discharge area (4).

9 Claims, 8 Drawing Sheets

PORTABLE DEVICE FOR TREATING INSECT BITES AND THE LIKE

The present invention has for its subject a portable device for treating the bites or stings of insects and harmful creatures.

As is well-known, in the event of bites or stings by insects or other creatures which transmit poisons or toxins, it is possible to carry out a local treatment in the area of the bite or sting for the purpose of degrading the poison or toxin which has been injected, by subjecting them to a suitable electrical discharge.

In particular, there are treatment devices known which exploit the piezoelectric effect to generate this electrical discharge: in these devices, the operator (who may be the same person as the victim of the bite or sting), acts on a piezoelectric crystal, usually by means of a more or less direct mechanical control, imposing a "state of stress" on the crystal, which reacts by generating a difference in potential. By connecting the two poles of the crystal to suitable terminals, and positioning these terminals in proximity to the area of the bite or sting on the victim, it is thus possible to discharge this difference in potential in the area itself, thus acting on the toxins or poisons injected.

The present applicant has designed a device of this kind, as described and claimed in patent EP0788809: this device has an upper control button, a piezoelectric crystal subject to the upper control button and a discharge area suitably positionable over the area to be treated.

All the components just listed are contained in a shell of a material which may be electrically conductive or non-conductive, according to the version, and which in the constructional solution implemented is made up of two longitudinal half-shells and two end portions, of which one is shaped in such a way as to be able to house and guide the control button, while the other is positioned in proximity to the discharge zone.

The device which has been briefly explained, although it is of proven efficacy and has been on the market for some time, has a number of disadvantages in the production stage.

Indeed, the complex construction of the shell entails a considerable and prolonged labor to assemble it, which has to provide for bringing together and aligning numerous pieces as well as the problematic coupling (for example by gluing or snapping together or ultrasound welding) of the two longitudinal half-shells of the containing body.

The long and onerous assembly process, which moreover entails difficulties of automation and must provide for the insertion and alignment of the piezoelectric element, the discharge area (with the relative terminals) and the control button, increases the labor time and in the last analysis the costs of production.

Furthermore, the very fact that two separate half-shells are involved entails the possibility that pieces with slightly different shades of color could be assembled together (as a result for example of different storage conditions or the two half-shells coming from different molding batches), thus resulting in a product of inferior overall quality.

An object of the present invention is to create a portable device for treating the bites or stings of insects and harmful creatures, capable of obviating the disadvantages just presented.

In particular, the present invention proposes to design a device which can be assembled more easily and quickly, at the same time ensuring the correct positioning of the components capable of generating the treating electrical discharge.

The present invention also has the object of allowing the production of a device with high and repeatable quality standards, avoiding as far as possible any lack of homogeneity in the appearance or exterior shape of the device itself.

Finally, the present invention is intended to achieve for the device under consideration the objective of reducing production costs and at the same time achieving better ergonomic performance, portability and practicality in use.

These and other objects are achieved by a portable device for treating the bites or stings of insects and harmful creatures in accordance with the present invention, having the characteristics set forth in the accompanying claims and illustrated below in two exemplary, but not for this reason limiting, embodiments, and also in the attached drawings, in which:

Figure 1:
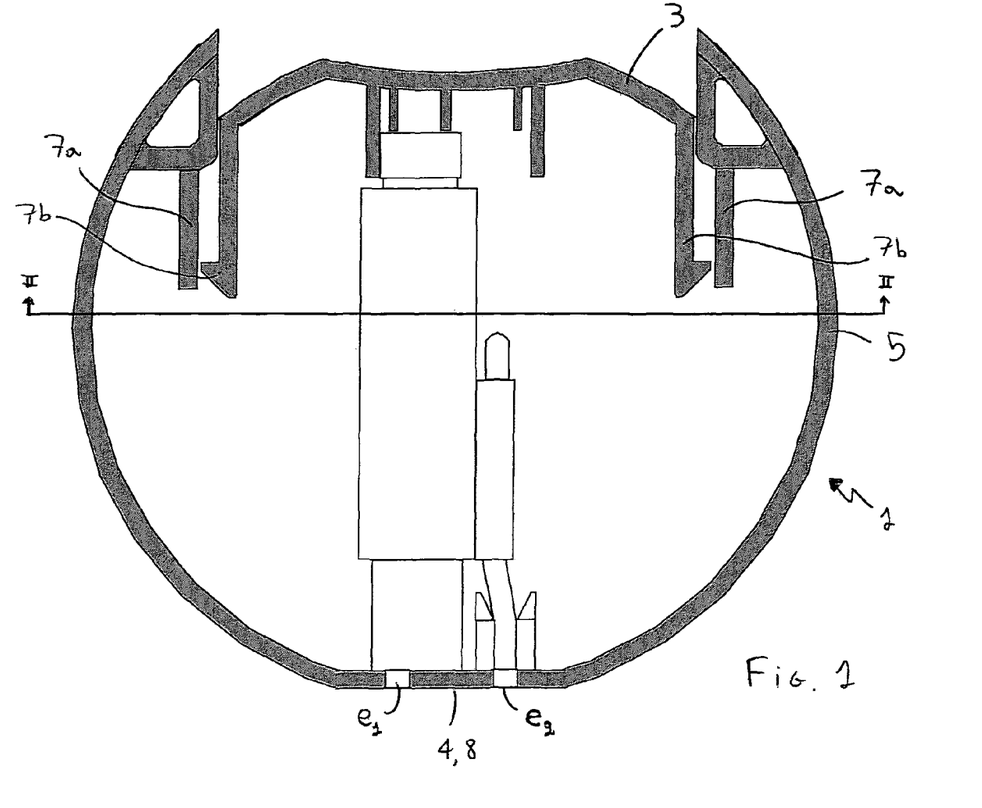
FIG. 1 shows a frontal view in section of a first embodiment of the device according to the invention.
Figure 2:
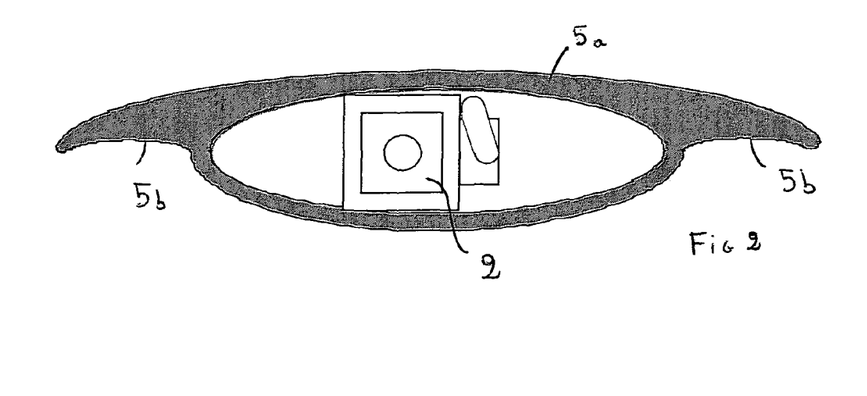
FIG. 2 shows a top view in section along the line II-II of the device shown in FIG. 1.
Figure 3:
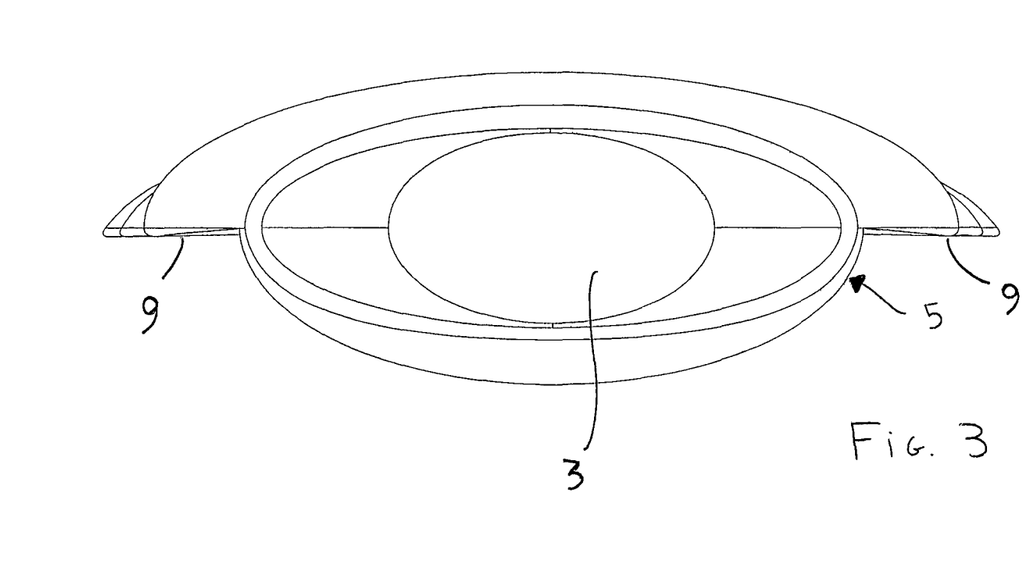
FIGS. 3, 4a and 4b show top views of several. variant embodiments of the device according to the invention.
Figure 4A:
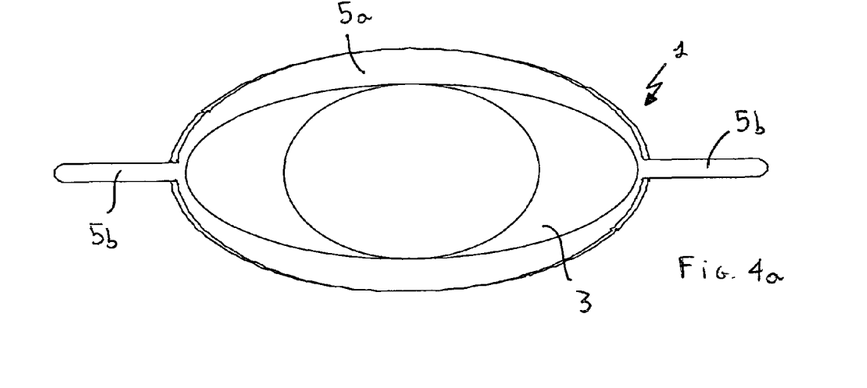
Figure 4B:
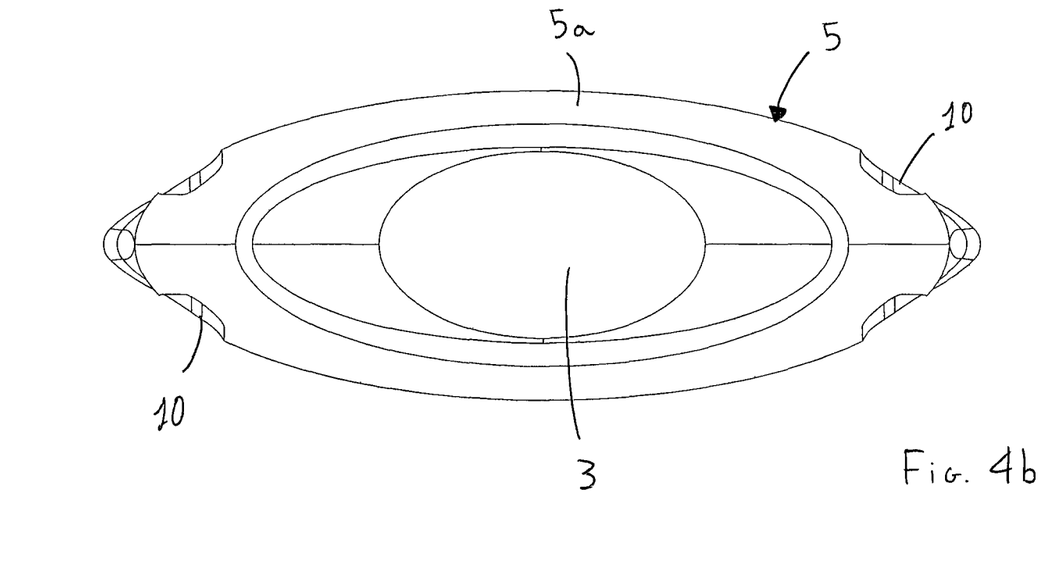
Figure 5A:
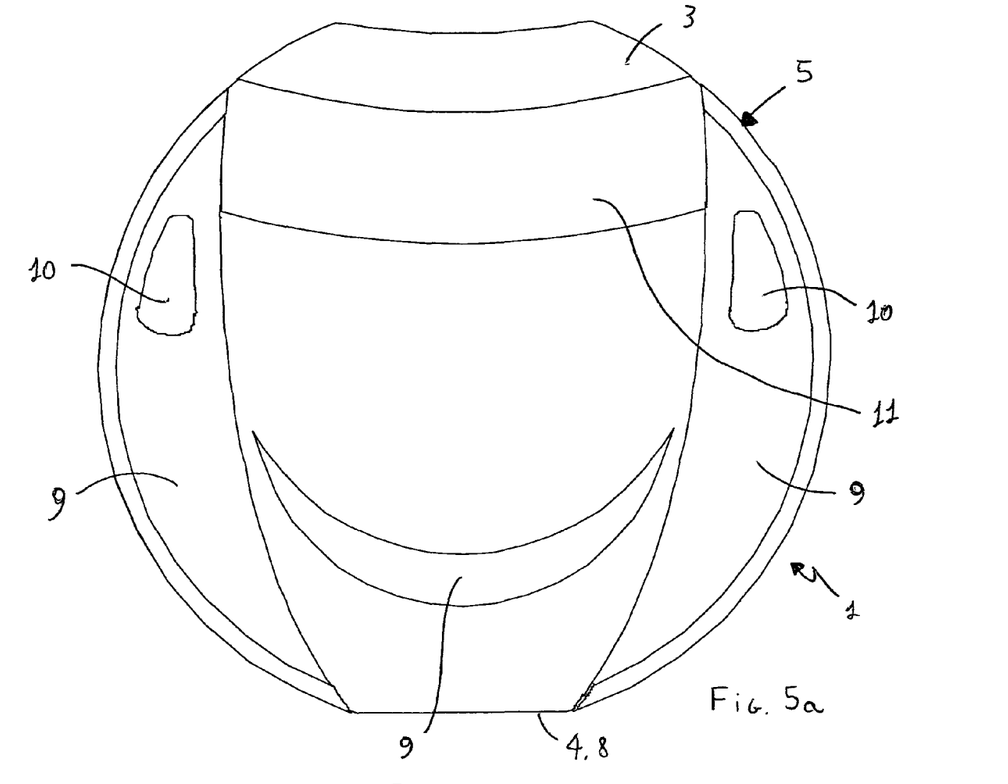
FIGS. 5a and 5b show front views of several variant embodiments of the device according to the invention.
Figure 5B:
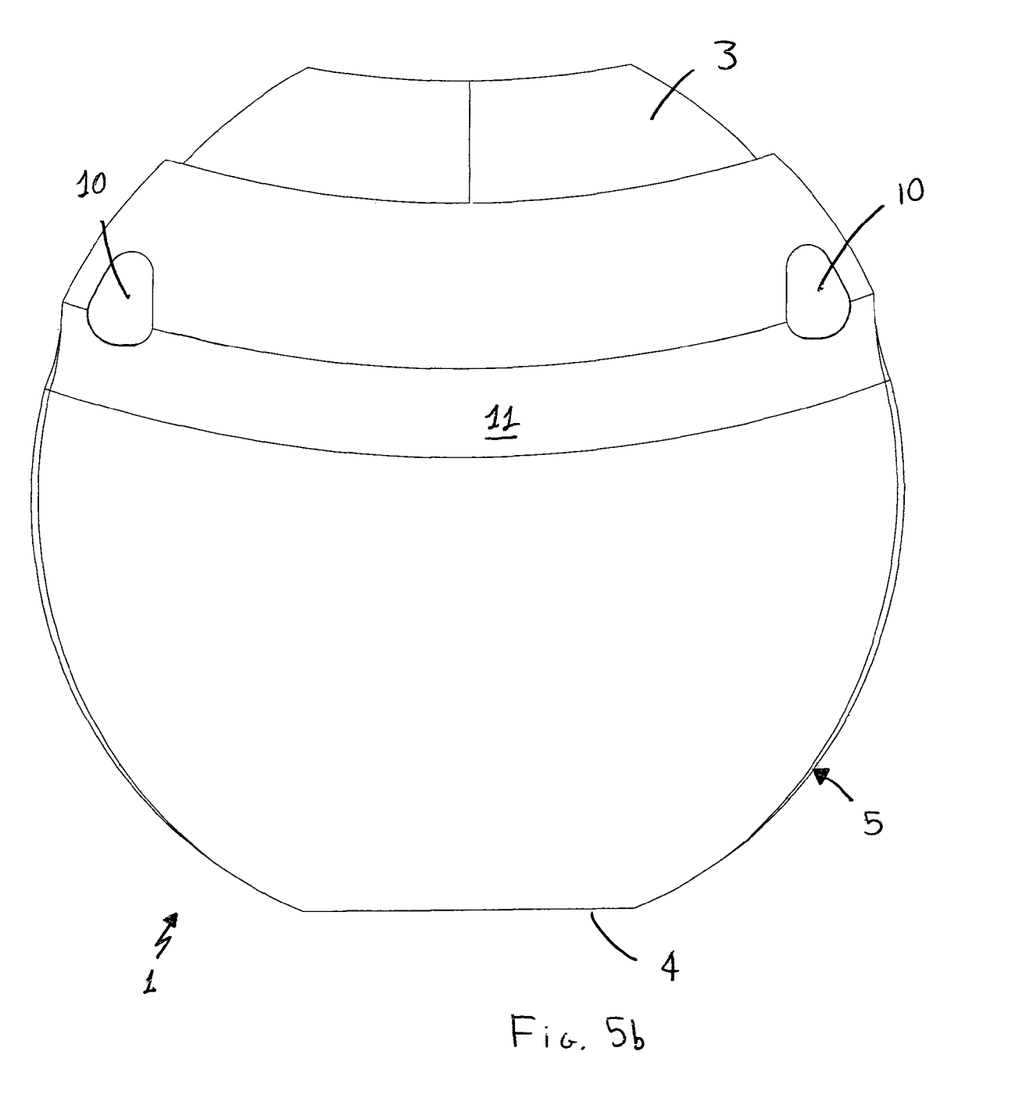
Figure 6:
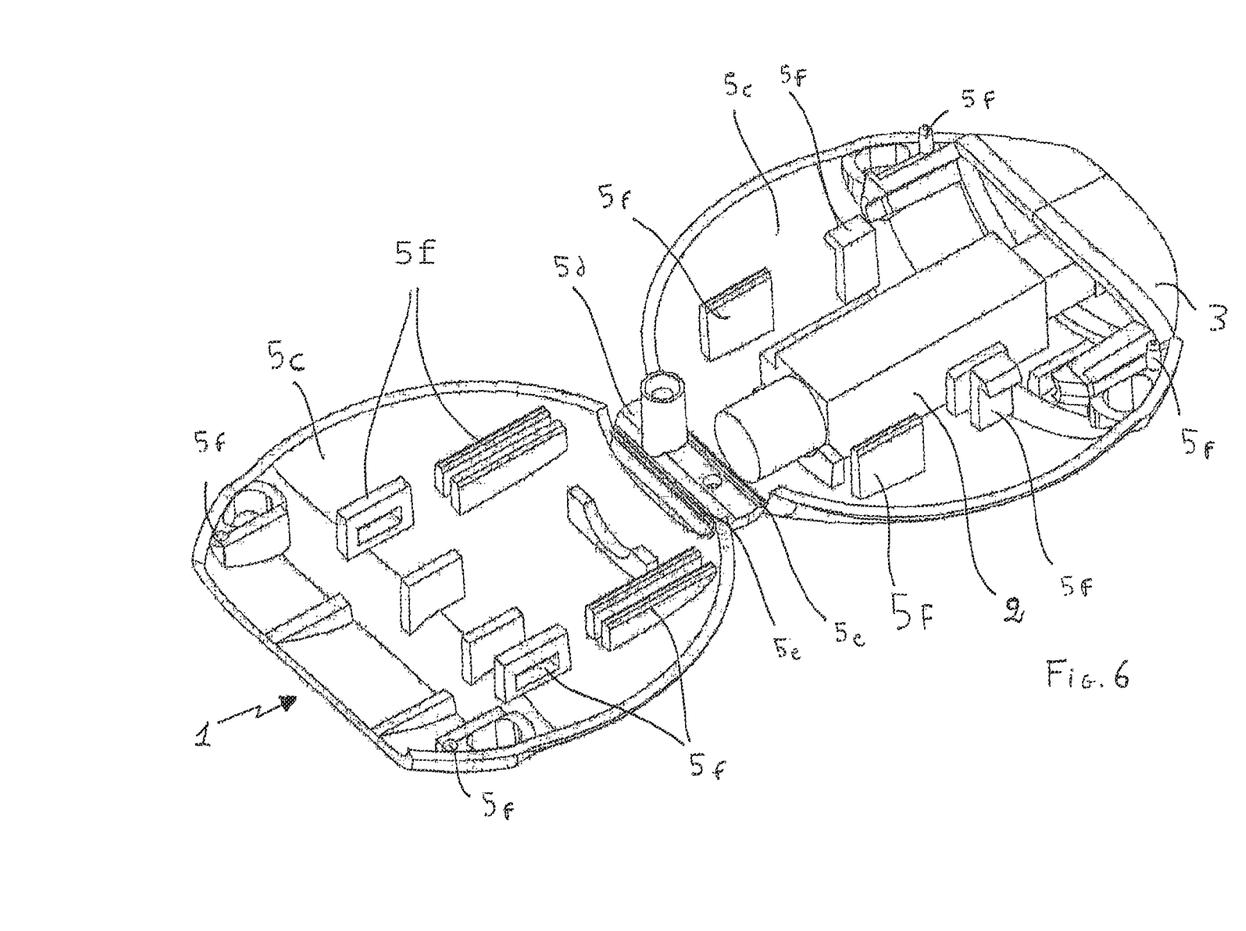
FIG. 6 shows a perspective view of a second embodiment of the device according to the invention in a half-assembled configuration.
Figure 7:
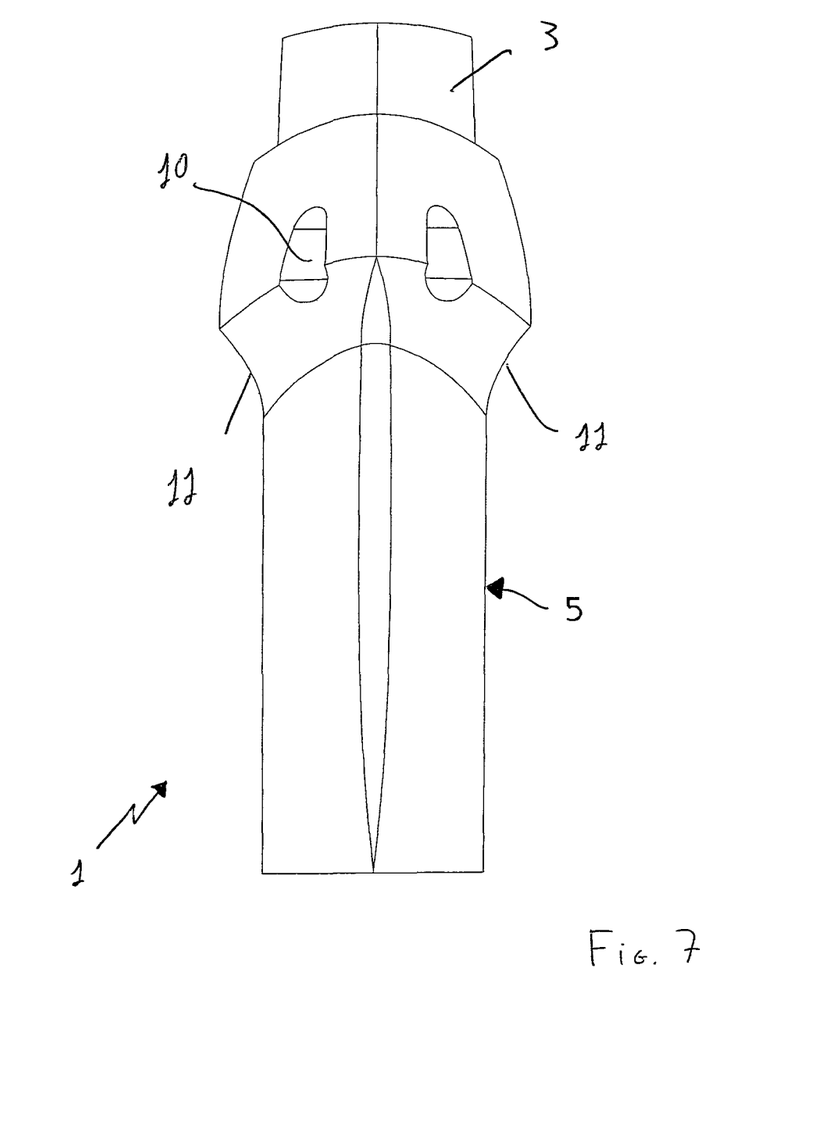
FIG. 7 shows a lateral view of the device shown in FIG. 6.
Figure 8:
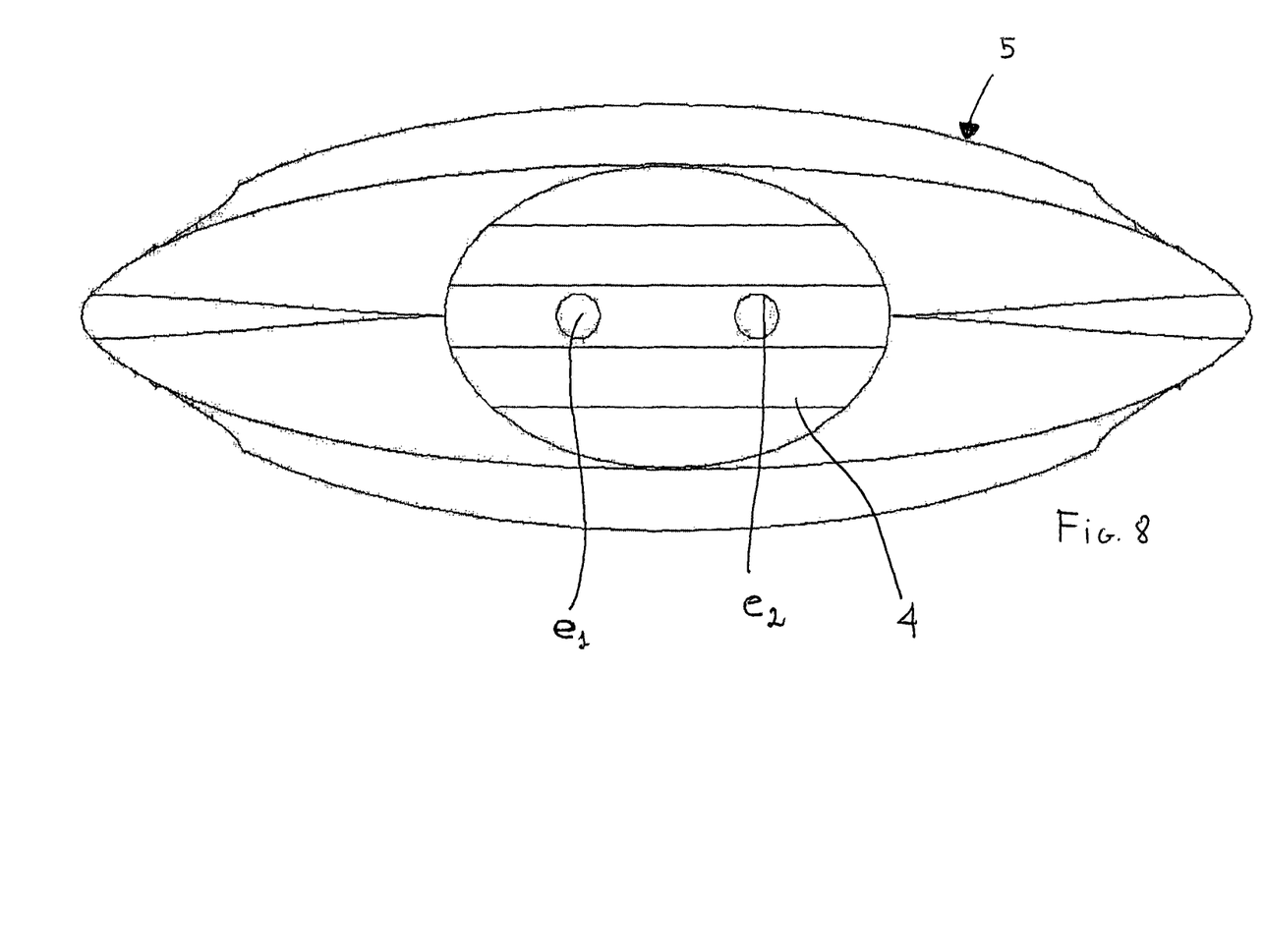
FIG. 8 shows a bottom view of a device according to the invention.

With reference to the attached drawings, the portable device for treating the bites or stings of insects and harmful creatures according to the invention is generally indicated by the number 1 and substantially comprises a piezoelectric element 2 capable of producing a predetermined difference in electrical potential, an actuating element 3 operable by a user and coupled to the piezoelectric element 2 in order to impart to it at least one predetermined state of stress/deformation and a discharge area 4 electrically connected to the piezoelectric element 2 and positionable in proximity to an area of a patient which has been bitten/stung in order to impart to it an electrical discharge generated by the above-mentioned difference in electrical potential.

Structurally, it should be observed that the piezoelectric element 2 forms two electrical poles (which may otherwise be referred to as ends or electrodes, marked $e_1$ and $e_2$ in the attached drawings), and in the discharge area 4 in turn, two polarized portions are created, which are respectively connected to one of these electrical poles.

Conveniently, the material and the shape of the polarized portions, as well as the modalities of their electrical connection to the poles of the piezoelectric element 2 may be of any kind whatever, provided that they are suitable for making an adequate electrical discharge (of appropriate voltage and amperage) circulate under the skin, in the area of the bite or sting.

Still from a structural point of view, we should note the presence of a containing body 5, which is advantageously monolithic and is capable of housing the piezoelectric element 2, the actuating element 3 and the discharge area 4.

In other words, in this embodiment the containing body 5 is made in a single piece and creates an internal housing space 6: this internal housing space is intended to at least partially house the piezoelectric element 2.

In order to ensure the correct inter-operability of the various structural components presented above, the containing body 5 has a guide and housing portion 7 capable of receiving the actuating element 3: in more detail, this guide and housing portion 7 has at least one sliding guide 7a, engageable by the actuating element 3 (which for its part has suitable insertion and guide counterparts 7b, such as for example the teeth illustrated in the attached drawings, which are snapped into place in their respective sliding guides 7a at the time of assembling device 1 and remain stably channeled there during the use of the actuating element by an operator).

The containing element 5 also has an operating portion 8 substantially corresponding to the discharge area 4: in other words, a suitable portion of the external surface of the containing body 5 coincides with the area for pressing on the zone where the bite or sting has been inflicted.

From an ergonomic point of view, it should be observed that the preferred (but not exclusive) embodiment described here has an architecture in which the piezoelectric element 2, the actuating element 3 and the discharge area 4 are mutually aligned along an identical operating axis: this operating axis is conveniently the axis of symmetry of the containing body (5).

In any event, if the constructional needs of the moment require it, the piezoelectric element 2 can also not be positioned exactly on this axis but slightly displaced or offset with respect to the axis of symmetry of the containing body 5: in particular, the offset arrangement of the piezoelectric element can be implemented in such a way that the two ends or electrodes or poles are centered, equidistantly for example, around the axis of symmetry of body 5.

Still with reference to the attached drawings, it may also be noted that the containing body 5 includes a primary portion 5a forming within itself said housing space 6 and at least one secondary portion 5b adjacent to this primary portion 5a: the conformation and the arrangement of the latter secondary portion 5b can be designed so as to respond to various ergonomic and structural robustness requirements of device 1.

With reference to the attached drawings, it may for example be seen that the containing body 5 includes two secondary portions 5b arranged symmetrically on opposite sides with respect to the primary portion 5a: in this way it is possible simultaneously to provide a better grip for the user, and at the same time to achieve a high degree of rigidity and structural integrity, all favoring the possibility of exercising the appropriate mechanical pressure on the actuating element without incurring the risk of structural failure of the rest of the device itself.

Again in order to endow the device with greater precision and ease of manipulation, there are also ergonomic interfacing surfaces 9 and/or 11, which are located externally on the primary portions 5a and/or secondary portions 5b and are conveniently capable of improving the grip and/or the manipulation of device 1 on the part of a user.

In order to be able to provide device 1 with carrying straps or similar, there can finally be one or more connecting slots 10, formed in connecting body 5 and located in any position, provided that they are suitable for being connected to a thread-like or ribbon-like or chain-type element or similar means. A particularly practical example is to connect the product to a key ring by means of a slot 10 so as to have the product always within reach and ready for use.

In a second embodiment of the present invention, the containing body 5 includes a monolithic shell reversibly or irreversibly configurable between an assembly condition in which it allows the insertion of the piezoelectric element 2 and/or the actuating element 3, and an operating condition in which it creates the housing space 6.

As may be seen in the attached drawings, the containing body 5 may be made up of two lobes 5c, respectively counter-profiled, joined without breach of continuity and by mutually opposed parts, to a connecting section 5d.

More particularly, it may be seen that connecting section 5d includes one or more pliable portions 5e (or in other words pre-programmed folding lines) which allow the two lobes 5c to be brought together, thus constituting the operating condition of the containing body 5.

Operationally, the closure of the two lobes 5c (and therefore the creation of the housing space 6) is ensured by suitable connection means: for example, it is possible to provide snap and/or mortise closure means 5f, which are operationally activated between the two lobes 5c, preferably after the insertion of the piezoelectric element 2 and/or the actuating element 3.

From the point of view of the assembly procedure, snap closure means do not require ultrasound welding or gluing, and by contrast with a simple mortise closure they ensure that the joint holds together even in the event of a fall (thus avoiding the possibility, in the event that the whole object 1 is accidentally dropped, of small fragments of the internal mechanism being scattered in uncontrolled manner into the environment).

From the point of view of the choice of materials, it is possible to make the containing body 5 and/or the actuating element 3 entirely or partially out of conductive material (for example conductive plastic, or plastic coated with a conductive treatment such as chroming, nickel plating, gold plating or many others). This means that only one electrode is necessary, because one of the two poles of the device (typically the negative pole) is constituted by the containing body 5 itself, while the electrical circuit which allows the electrical discharge to be sent through the zone to be treated is closed through the hand of the operator/patient grasping the device 1, and more precisely is closed by passing through the arm and body of the user as far as the application point of the apparatus to the area of skin to be treated.

When made of electrically conductive material, the containing body 5 and/or the actuating element 3 function in practice as electrode(s), so as to allow the passage of an electrical discharge.

At all events, in order to avoid "short circuit" problems in the discharge area 4 (i.e. in order to avoid the electrical discharge passing directly from one electrical pole to the other on device 1, without penetrating the patient's skin), electrically insulating means can be provided in proximity to at least one of the two electrodes or electrical poles connected to the piezoelectric element 2 (for example, located around the wire which constitutes the positive pole).

It should be noted that, irrespective of the material of which the various parts of device 1 are made, the two electrodes or electrical poles can either consist of point (or discrete) areas positioned at a certain relative distance on the discharge area, or consist of a combination of a single point or discrete electrode/pole and a given portion of (typically external) surface of the containing body 5 and/or of the actuating element 3: this external surface portion will from time to time be the portion of the device actually in contact with the operator's skin.

In any event, it is also possible to make the containing body 5 and/or the actuating element 3 (or more generally, all the parts of the device which come into direct contact with the operator's skin) in electrically insulating material.

In this alternative embodiment it is therefore desirable for the electrical discharge generated by the piezoelectric element 2 to be carried to the tips of the two electrodes located in the discharge area 4.

According to the type and the arrangement of the electrodes (in point or distributed form), the mode of transmitting/propagating the electrical discharge into the patient's body varies: in fact, by using point or discrete electrodes, this electrical discharge will be propagated superficially over the area to be treated (and more particularly within a zone immediately adjacent to the electrodes themselves), while when one of the two poles/electrodes consists of at least one part of the actuating element 3 and/or of the containing body 5, the electrical discharge will travel into the patient's body (passing first through the arm and the hand which has activated the actuating element 3 and/or which holds the device, through the containing body 5 and returning to the device 1 in proximity to the subcutaneous zone corresponding to the area to be treated.

According to this last mode of propagation, the electrical discharge reaches the zone pervaded by the toxin and/or poison with greater efficacy, thus exercising its effects at depth.

Still according to this last mode of propagation, it is clear that if the operator of the device 1 does not coincide with the patient, the operator himself/herself must arrange to close the electrical circuit with the patient, for example by touching the latter.

In accordance with the present invention it is advantageously possible to implement a new and original assembly method: this method requires first of all the provision of a monolithic shell (which conveniently includes two lobes and a connecting section and which will be configurable as above), of a piezoelectric element and an actuating element, and secondly requires the positioning of these last pieces inside a housing space created by the containing body itself.

In particular, the present method requires that the step of the creation of the above-mentioned containing space should take place by bringing the two lobes together at least in proximity to the actual connecting section which joins them.

According to the needs of the moment, the creation of the containing space can take place before, simultaneously with or after the positioning of the actuating element and the piezoelectric element.

The method just explained is implementable on the second variant embodiment of the device according to the present invention: in any case, the step of the creation of the housing space can even be activated, in the first embodiment of the device, for example by the injection-molding of a monolithic shell or similar process.

The invention enables important advantages to be achieved.

First of all, it should be noted that the peculiar constructional architecture of the containing shell enables the achievement of a significant reduction in production times, accompanied by an equally significant reduction in the complexity of the assembly operation: indeed, thanks to the "one-piece" conformation of the shell and the appropriate provision of the housing space, the positioning and alignment of the piezoelectric element and the other sub-components associated with it are extremely quick and precise, and can actually be performed by a single operator (or indeed be automated).

In other words, the present invention achieves a considerable improvement in the production process, avoiding involvement in complex and delicate operations of coupling several parts of the containing shell.

Secondly, it should be noted that the provision of the monolithic shell enables problems of poor quality in the alignment and assembly of two or more half-shells to be avoided, and at the same time avoids the manufacture of finished products in which the different parts of the shell are of different shades of color.

Finally, it should be noted that the present invention allows the creation of a portable device for treating the bites or stings of insects and harmful creatures with low costs of production and sale, and at the same time makes the object itself easier for the end user to manipulate and carry.

The invention claimed is:

1. A portable device for treating the bites or stings of insects and harmful creatures, comprising:
    a piezoelectric element configured for producing a predetermined difference in electrical potential;
    an actuating element operable by a user and associated with said piezoelectric element to impart to the piezoelectric element a predetermined state of stress;
    a discharge area electrically connected to the piezoelectric element and positionable in proximity to an area of a patient which has been bitten/stung in order to impart to the patient an electrical discharge generated by said difference in electrical potential;
    a monolithic containing body configured for housing the piezoelectric element, the actuating element and the discharge area, the monolithic containing body comprising a monolithic shell configurable between an assembly condition allowing the insertion of the piezoelectric element and/or the actuating element, and an operating condition defining a housing space, the monolithic containing body comprising a connecting section ($5d$), a first lobe ($5c$) and a second lobe ($5c$) joined without breach of continuity, the connecting section ($5d$) including a first pliable portion ($5e$) connecting the connecting section ($5d$) to the first lobe ($5c$), the connecting section ($5d$) including a second pliable portion ($5e$) connecting the connecting section ($5d$) to the second lobe ($5c$), each pliable portion ($5e$, $5e$) providing a folding line effective to permit the first and second lobes ($5c$, $5c$) to be folded together so as to create said operating condition, the connecting section ($5d$) having at least one through hole containing a polarised portion which is electrically connected to the piezoelectric element.

2. A device according to claim 1, characterised in that the containing body has a guide and housing portion configured for receiving the actuating element and in that said guide and housing portion has at least one sliding guide engaged by the actuating element, the actuating element comprising at least one insertion and guide counterpart configured for being inserted into a respective sliding guide.

3. A device according to claim 1, characterised in that the piezoelectric element, the actuating element and the discharge area are mutually aligned along the same operating axis, said operating axis being an axis of symmetry of the containing body.

4. A device according to claim 1, also comprising at least one connecting slot formed in the containing body.

5. A device according to claim 1, also comprising connecting means, selected from the group consisting of snap and mortise closure means, operationally activatable between said lobes, after the insertion of the piezoelectric element and the actuating element.

6. A device according to claim 1, characterised in that the containing body and the actuating element are made at least partially of electrically non-conductive material.

7. A device according to claim 1, characterised in that the containing body and the actuating element are made at least partially of electrically conductive material, the containing body and the actuating element being electrodes to allow the passage of an electrical discharge.

8. A device according to claim 1, wherein the connecting section is provided with two polarised portions in the form of two through holes internally connected with two electrodes of the piezoelectric element and externally intended to be positioned in contact with the area of a patient which has been bitten/stung.

9. A device according to claim 1, wherein said connecting section, on its internal side, is flat and configured for being in direct contact with two electrodes of the piezoelectric element.

* * * * *

UNITED STATES PATENT AND TRADEMARK OFFICE
CERTIFICATE OF CORRECTION

| | | |
|---|---|---|
| PATENT NO. | : 8,712,555 B2 | Page 1 of 1 |
| APPLICATION NO. | : 12/514521 | |
| DATED | : April 29, 2014 | |
| INVENTOR(S) | : Bellifemine | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this
Twenty-first Day of July, 2015

Michelle K. Lee
*Director of the United States Patent and Trademark Office*